United States Patent [19]

Lokken

[11] Patent Number: 4,608,088
[45] Date of Patent: Aug. 26, 1986

[54] DENTURE ADHERENT POWDER

[75] Inventor: Oddvin Lokken, Rye, N.Y.

[73] Assignee: Dento-Med Industries Incorporated, North Miami Beach, Fla.

[21] Appl. No.: 592,116

[22] Filed: Mar. 22, 1984

[51] Int. Cl.⁴ .............................................. C09K 3/00
[52] U.S. Cl. ..................................... 106/35; 106/209; 523/109; 523/120
[58] Field of Search ................ 106/209, 35, 205, 208, 106/197 C; 523/120, 109

[56] References Cited

U.S. PATENT DOCUMENTS

| | | | |
|---|---|---|---|
| Re. 23,700 | 8/1953 | Lochridge | 106/35 |
| 2,249,694 | 7/1941 | Wilding | 106/35 |
| 2,345,255 | 3/1944 | Gross | 106/35 |
| 2,390,137 | 12/1945 | Vallandigham | 106/35 |
| 2,397,145 | 3/1946 | Joy | 106/35 |
| 2,422,497 | 6/1947 | Noyes | 106/35 |
| 2,424,895 | 7/1947 | Noyes | 106/35 |
| 2,425,118 | 8/1947 | Noyes | 106/38.5 |
| 2,657,971 | 11/1953 | Lochridge | 106/197.2 |
| 2,733,156 | 1/1956 | Cornell et al. | 106/38.4 |
| 2,878,129 | 3/1959 | Rabchuk | 106/38.4 |
| 3,010,834 | 11/1961 | Crowell | 106/35 |
| 3,246,998 | 4/1966 | Higashi et al. | 106/35 |
| 3,764,707 | 10/1973 | Habersberger | 106/208 |
| 4,001,151 | 1/1977 | Keegan | 523/120 |
| 4,318,742 | 3/1982 | Lokken | 106/35 |
| 4,381,947 | 5/1983 | Pellico | 106/35 |
| 4,394,172 | 7/1983 | Scheuble et al. | 106/209 |
| 4,468,484 | 8/1984 | Pellico | 524/28 |
| 4,515,913 | 5/1985 | Pellico | 106/35 |

OTHER PUBLICATIONS

Industrial Gums, Whistler, R. L., pp Academic Press, New York & London, 1973.
The Science of Dental Materials-pp. 71-72.

*Primary Examiner*—Theodore Morris
*Attorney, Agent, or Firm*—Jacobs & Jacobs

[57] ABSTRACT

A denture adherent preparation in powder form, which comprises an admixture of
(a) from about 40-60% dental adhesive
(b) from about 60-4% gel-forming mixture of a water-soluble alginate and a setting agent for the water-soluble alginate in an amount effective to cause gelation of an aqueous solution containing the water soluble alginate.

The powder composition of the present invention comprising the gel-forming mixture and dental adhesive described above, may also be used as a depot formulation for delivery of therapeutic agents to the oral cavity.

9 Claims, No Drawings

DENTURE ADHERENT POWDER

The present invention relates to denture adherent preparations, and more particularly to denture adherent powders.

Denture adherent preparations are in extensive use. These preparations are intended to securely hold the dentures in place, both at rest and during mastication. It has been reported in the dental literature that the use of a denture adherent will make the user of full dentures act in a natural way in his social environment, something that he may apprehend as difficult without the security delivered by the adhesive. Drs. Tarbert and Grossman, J.A.D.A., 101, November, 1980, 789-791, report that the use of a denture adherent preparation does not increase mucosal irritation and, in fact, can reduce the likelihood of such irritation.

A wide variety of denture adhesives are used in denture adherent preparations. The present invention is based upon the use of a two component denture adherent preparation comprising a denture adhesive and a gel-forming component in intimate admixture. When the preparation according to the present invention is mixed with water, the gel-forming component forms a water-insoluble gel matrix having dispersed therein the denture adhesive. The gel-forming matrix itself does not have denture adhesive properties and is used as a matrix for the denture adhesive.

According to the present invention, the gel-forming matrix component comprises a mixture of a water-soluble alginate, a setting agent for the water-soluble alginate in an amount effective to cause gelation of an aqueous solution containing the water soluble alginate and, if desired, a retarder and/or a filler. It will be recognized that the gel-forming matrix component is a material known per se as a dental impression compound. Thus, irreversible hydrocolloid impression material based upon the use of water-soluble alginates is well described in the literature and is commercially available as an impression compound. As described in U.S. Pat. Nos. 2,249,694, 2,390,137, 2,424,895 and 3,010,834, while alginic acid itself is insoluble in water, various water-soluble salts exist, such as the sodium, potassium, ammonium and magnesium alginates. The water-soluble alginates will dissolve in water and form a viscous sol that is not particularly useful as an impression material. However, the addition of a setting agent to the aqueous solution will cause an insoluble gel to form, the setting agent acting as a cross-linker. The known setting agents comprise salts of poly-valent metals, such as the salts of the metals of Group IIA, such as beryllium, calcium and strontium, Group IIB, such as zinc and cadmium, and of Group IIIA, such as aluminum.

A preferred material for use as the setting agent is calcium sulfate. If the dihydrate form is used, the reaction is known to proceed quite rapidly, whereas a slower gel-forming reaction takes place when the hemihydrate is used, and an even slower reaction rate is obtained with the anhydrate. If the gel-forming reaction occurs too quickly, as for example with the use of a setting agent of the type exemplified by calcium sulfate dihydrate, it is known that a retarder can be added to the gel-forming composition to retard the reaction rate. These retarders are salts having an anion that forms an insoluble or slightly soluble salt with the setting agent, such as the alkali metal phosphates, oxalates, carbonates, and citrates. As is known, the retarder will preferentially react with the setting agent to deprive the gel-forming solution of the cross-linking agent, and when the reaction between the setting agent and the retarder is completed, the setting agent is then free to react with the water-soluble alginate to form the insoluble gel.

As is known, fillers are optional ingredients of the gel-forming composition and are used to reduce tackiness and add strength. A wide variety of fillers have been proposed, such as silica, clay, kaolin, calcium carbonate, magnesium carbonate, titanium dioxide and the like.

As mentioned above, the gel matrix, when formed, does not act as a denture adherent. Indeed, a requirement of an impression compound is that it not adhere to the teeth and gums during the process of making the impression. It is therefore surprising to have discovered that an alginate gel impression compound can be used to advantage in a denture adherent preparation. In particular, the insoluble gel matrix acts as a means of holding the denture adhesive in place and to provide a cushioning effect on the denture tissue bearing surfaces. In addition, the insoluble gel permits the use of water-soluble denture adhesive materials, which would otherwise be impractical for use as a long lasting denture adherent. Thus, water-soluble denture adhesive materials are subject to attack by the saliva in the mouth, but their use in the insoluble gel matrix is not only possible, but actually preferred in many instances, since their dispersion in and throughout the insoluble gel acts to protect them from attack by the saliva, and in a sense, renders them insoluble.

Any denture adhesive may be used in the practice of the present invention. Thus, a water-soluble or water-insoluble, natural or synthetic gum may be used, as well as the natural and synthetic elastomers proposed for use in the denture adherent literature. Suitable natural gums include karaya gum, tragacanth gum, acacia gum, arabic gum, locus bean gum, guar gum, Shiraz gum, pectin and pectinates. Synthetic gums such as carboxymethylcellulose gums, cellulose sulfate gums and hydroxyethylcellulose may be used. Gums that are used in the preparation of chewing gum may also be employed, such as chicle, chicle gum, zapota gum, jelutong gum, and pontianak gum. Elastomeric materials such as butadiene-styrene rubber, butyl rubber, and polyisobutylene may be used. Other polymers may also be employed, such as polyethyleneglycol of higher molecular weight, polyvinylacetate, polyacrylamide as well as copolymers of acrylic acid and acrylamide, and the like. Food grade petrolium wax is another useful material.

It is presently preferred to use arabic gum and/or carboxymethylcellulose, and in particular, it is presently preferred to use a mixture of arabic gum and sodium carboxymethylcellulose. These denture adhesives provide excellent denture adhesion and are readily available.

U.S. Pat. No. 4,318,742 and the references cited therein provide an overview of the wide variety of denture adhesive materials that have been proposed for use in the literature and which are available for use in the present invention. The proportions of the gel-forming component and the denture adhesive component must be empirically determined for a given denture adhesive preparation. In general, the use of a water-soluble denture adhesive material will require the use of a larger amount of the gel-forming component than would the use of a water-insoluble denture adhesive. Generally, however, the gel-forming material will comprise from about 15% to about 85% of the composition according to the invention, and the denture adhesive component will comprise from about 85% to about 15% of the composition, all by weight. As is known, the denture adherent composition of the present invention may include auxiliary ingredients affecting the taste, color, or even the physical and chemical properties of the composition. Thus, colorants, flavorings, perfumes or other odorants, opacifiers and the like to improve the appearance of the composition, can be employed. In particular, flavorings are a desirable auxiliary material to make the use of the denture adherent composition more pleasant, and sugar, xylitol, glycerine or other natural or synthetic sweeteners and flavoring agents may be used for this purpose. Antibiotics and/or antifungal agents can also be employed if needed so as to prevent infection. Generally, the use of auxiliary materials will be not more than about 30% of the total weight of the composition, and generally not more than about 15% by weight.

Useful ranges for the components of the present invention are set forth below:

|  | Parts by Weight | |
| --- | --- | --- |
|  | Preferred | Most Preferred |
| Water-soluble alginate | 5–50 | 10–20 |
| Setting agent | 1–30 | 5–20 |
| Retarder | 0–30 | 0.5–15 |
| Filler | 0–40 | 5–20 |
| Denture adhesive | 20–80 | 40–60 |
| Auxiliary agent | 0–30 | 0.5–15 |

A useful formulation in the practice of the present invention is as follows:

| Preferred Formula | Parts By Weight |
| --- | --- |
| Potassium alginate | 15 |
| $CaSO_4.2H_2O$ | 12 |
| $Na_3PO_4$ | 2 |
| Diatomaceous earth | 20 |
| Carboxymethylcellulose, sodium | 25 |
| Arabic gum | 25 |
| Flavoring, colorant. | 1 |
|  | 100 |

The denture adherent composition according to the present invention is used as follows. First, the dentures will by cleaned, since clean surfaces provide optimum bonding to the denture adhesive material. While the dentures are still wet, a quantity of the denture adherent preparation according to the present invention is sprinkled on to the tissue bearing surfaces of the denture, and the dentures are then inserted into the mouth. The user will be instructed to bite down gently for a few moments and not to eat for four to five minutes after use. When the composition according to the present invention is contacted with water, the insoluble gel is formed, trapping the denture adhesive material therein. The dentures are then securely held in place by the denture adhesive material and the insoluble gel will provide the additional advantage of the cushioning effect described above. If the dentures have deviated from their initial, proper fitting, then the user is best advised to have new dentures prepared with a proper fit. During the time when the new dentures are being prepared, the user can apply a first quantity of the composition according to the invention to the dentures as described above and then, rather than placing them in the mouth, the dentures can be held under a gentle stream of water to thoroughly wet the composition of the present invention, whereafter a second quantity of the composition is applied and then the dentures are placed in the mouth and the procedure described above is followed. This will provide a thicker layer of the set gel, which carries the denture adhesive material.

The composition of the present invention is suitably prepared by admixing the powders comprising the gel-forming component, and the denture adhesive component, in any suitable dry-blending equipment. As is known, the use of finely ground powder is desirable, since such powders rapidly react to form the denture-adherent composition and have a pleasant "feel" in the mouth. Generally, suitable powders will pass through a 10 mesh screen, and will preferably pass through a 40 mesh screen. Micronized powders are also suitable, such as those substantially all less than 100 mesh, preferably less than 200 mesh. In general, however, the particle sizes customarily employed in denture adherent preparations may be used to advantage in the practice of the present invention.

The present invention is illustrated in more detail in the Example that follows. In this Example and in the specification and claims of the present application, all percentages and parts and proportions are by weight, unless otherwise noted.

EXAMPLE

The following formulations are illustrative of the present invention, in addition to the formulation described above:

|  | Parts by Weight |
| --- | --- |
| Potassium alginate | 15.5 |
| $CaSO_4.2H_2O$ | 12 |
| $Na_3PO_4$ | 2 |
| Diatomaceous earth | 20 |
| Carboxymethylcellulose | 10 |
| Arabic gum | 40 |
| Flavoring, colorant | 0.5 |
|  | 100 |
| Sodium alginate | 20 |
| $CaSO_4.2H_2O$ | 15 |
| $Na_3PO_4$ | 3 |
| Silica | 1.5 |
| Tragacanth gum | 60 |
| Flavoring, colorant | 0.5 |
|  | 100 |
| Potassium alginate | 10 |
| $CaSO_4.2H_2O$ | 8 |
| $Na_3PO_4$ | 2 |
| Diatomaceous earth | 40 |
| Hydroxyethylcellulose | 20 |
| Methylcellulose | 20 |
|  | 100 |

The powder composition of the present invention comprising the gel-forming mixture and dental adhesive described above, may also be used as a depot formulation for delivery of therapeutic agents to the oral cavity. In this embodiment of the invention, the powder composition comprising an admixture of the dental adhesive and the gel-forming mixture will also include a therapeutically effective amount of a non-toxic, therapeutically active agent, such as a local anaesthesic, an analgesic, an antibiotic, an antiseptic or germicide, a fluoride compound and the like. Any therapeutic agent that is topically applied to the surface of the oral mucosa, to the surface of a tooth or to the interior of a tooth may thus be employed to advantage in the powder composition of the invention.

When admixed with water, the insoluble gel will entrap the dental adhesive as well as the therapeutic agent, and the dental adhesive will secure the composition to the oral mucosa and/or exterior or interior of the tooth being treated, thereby holding the composition in place during the time when the therapeutic agent is being released from the composition. The therapeutic agent will be used in a therapeutically effective amount customarily employed for the particular agent being used, but generally the therapeutic agent will be from about 0.5 to about 200%, preferably from about 0.5 to about 100% by weight, based on the total weight of the powder composition of the present invention.

I claim:

1. A denture adherent preparation in powder form, which comprises an admixture of
   (a) from about 40% to about 60% of a dental adhesive; and
   (b) from about 60% to about 40% of a gel-forming mixture comprising from about 10 to about 20% of a water-soluble alginate, from about 5 to about 20% of a setting agent for the water-soluble alginate, from 0.5 to about 15% of a retarder and from about 5 to about 20% of a filler; all percentages being based on the total weight of the composition.

2. The preparation according to claim 1, wherein said dental adhesive comprises a natural or synthetic gum or a mixture thereof.

3. The preparation according to claim 1, wherein said water-soluble alginate is sodium or potassium alginate.

4. The preparation according to claim 1, wherein said setting agent is calcium sulfate dihydrate, calcium sulfate hemihydrate or calcium sulfate anhydrate or a mixture thereof.

5. The preparation according to claim 1, wherein said retarder is an alkali metal salt having an anion that forms an insoluble or slightly soluble salt with the setting agent.

6. The preparation according to claim 1, including from 0.5 to 15% of an auxiliary agent, based on the total weight of the composition.

7. A denture adherent preparation in powder form, which comprises:

|  | Weight Percent |
| --- | --- |
| Potassium alginate | 15 |
| $CaSO_4.2H_2O$ | 12 |
| $Na_3PO_4$ | 2 |
| Diatomaceous earth | 20 |
| Carboxymethylcellulose, sodium | 25 |
| Arabic gum | 25 |
| Flavoring, colorant. | 1 |

8. The preparation according to claim 1, wherein said dental adhesive is a mixture of karaya gum and sodium carboxymethylcellulose.

9. The preparation according to claim 2, wherein said natural gum is selected from the group consisting of karaya gum, tragacanth gum, acacia gum, arabic gum, locus bean gum, guar gum, Shiraz gum, pectin, pectinates, chicle gum, zapota gum, jelutong gum, and pontianak gum.

* * * * *